US010925771B2

(12) United States Patent
Lopath et al.

(10) Patent No.: US 10,925,771 B2
(45) Date of Patent: Feb. 23, 2021

(54) DEVICE FOR IRRADIATION OF THE EYE

(71) Applicant: TECLens, LLC, St. James, NY (US)

(72) Inventors: Patrick David Lopath, Stamford, CT (US); Edward Paul Harhen, Duxbury, MA (US); David L. Gershaw, Charlestown, MA (US); James Paolino, Somerville, MA (US); David E. Acker, St. James, NY (US)

(73) Assignee: TECLens, LLC, St. James, NY (US)

( * ) Notice: Subject to any disclaimer, the term of this patent is extended or adjusted under 35 U.S.C. 154(b) by 225 days.

(21) Appl. No.: 15/538,328

(22) PCT Filed: Dec. 21, 2015

(86) PCT No.: PCT/US2015/067087
§ 371 (c)(1),
(2) Date: Jun. 21, 2017

(87) PCT Pub. No.: WO2016/106210
PCT Pub. Date: Jun. 30, 2016

(65) Prior Publication Data
US 2017/0367879 A1 Dec. 28, 2017

Related U.S. Application Data

(60) Provisional application No. 62/095,416, filed on Dec. 22, 2014.

(51) Int. Cl.
*A61F 9/00* (2006.01)
*A61F 9/009* (2006.01)
(Continued)

(52) U.S. Cl.
CPC .............. *A61F 9/009* (2013.01); *A61N 5/06* (2013.01); *G02B 6/2808* (2013.01); *G02C 7/04* (2013.01);
(Continued)

(58) Field of Classification Search
CPC .......... A61F 2009/00872; A61F 9/0079; A61F 9/008; A61F 9/00804; A61F 9/009; A61B 18/20
See application file for complete search history.

(56) References Cited

U.S. PATENT DOCUMENTS

| 4,799,784 A * | 1/1989 | Safir | A61B 3/10 351/212 |
| 5,141,506 A * | 8/1992 | York | A61F 9/00804 128/898 |

(Continued)

FOREIGN PATENT DOCUMENTS

| DE | 19719728 A1 * | 11/1998 | .......... G02B 6/0006 |
| DE | 102010016629 A1 * | 10/2011 | .......... A61B 3/0008 |

(Continued)

OTHER PUBLICATIONS

International Search Report for Application No. PCT/US2015/067087 dated Apr. 1, 2016.
(Continued)

*Primary Examiner* — Rex R Holmes
*Assistant Examiner* — Sana Sahand
(74) *Attorney, Agent, or Firm* — Lerner, David, Littenberg, Krumholz & Mentlik, LLP

(57) ABSTRACT

A device for irradiation of the eye of a living subject with light such as UV light includes a structure (20) adapted to overlie the outer surface of the eye, the structure having an axis (28, 128) extending in a downward direction (D) towards the eye when the structure overlies the eye. A light scattering element (70, 158, 141) within the structure includes a peripheral portion remote from the axis and a central portion adjacent the axis. A plurality of transmission optical fibers (42, 157) in optical communication with the
(Continued)

peripheral portion of the light scattering element at a plurality of locations spaced around the axis.

19 Claims, 11 Drawing Sheets

(51) Int. Cl.
    *G02B 6/28*     (2006.01)
    *A61N 5/06*     (2006.01)
    *G02C 7/04*     (2006.01)
    *A61F 9/008*     (2006.01)

(52) U.S. Cl.
    CPC ..... *A61F 9/008* (2013.01); *A61F 2009/00872* (2013.01); *A61N 2005/063* (2013.01); *A61N 2005/0648* (2013.01); *A61N 2005/0661* (2013.01)

(56) References Cited

U.S. PATENT DOCUMENTS

| | | | |
|---|---|---|---|
| 5,437,658 A * | 8/1995 | Muller | A61F 9/00821 606/17 |
| 5,824,023 A * | 10/1998 | Anderson | A61B 18/203 607/88 |
| 6,221,028 B1 * | 4/2001 | Lieberman | A61B 3/0008 351/200 |
| 6,267,752 B1 * | 7/2001 | Svetliza | A61B 3/0008 600/205 |
| 2008/0208177 A1 | 8/2008 | Mrochen et al. | |
| 2012/0199995 A1 * | 8/2012 | Pugh | A61N 5/0618 264/1.36 |
| 2012/0209051 A1 * | 8/2012 | Blumenkranz | A61F 9/0017 600/2 |
| 2012/0310141 A1 | 12/2012 | Kornfield et al. | |
| 2014/0379054 A1 | 12/2014 | Cooper et al. | |

FOREIGN PATENT DOCUMENTS

| | | | |
|---|---|---|---|
| DE | 102010016629 B4 * | 11/2015 | ........... A61B 3/0008 |
| EP | 1642609 A1 | 4/2006 | |
| WO | WO-2011094758 A2 * | 8/2011 | ........... A61F 9/0079 |
| WO | 2011131180 A1 | 10/2011 | |
| WO | WO 2011131180 A1 * | 10/2011 | ........... A61B 3/0008 |
| WO | 2012112543 A2 | 8/2012 | |
| WO | 2015200817 A1 | 12/2015 | |

OTHER PUBLICATIONS

U.S. Appl. No. 61/839,016, filed Jun. 25, 2013.
U.S. Appl. No. 62/095,288, filed Dec. 22, 2014.

* cited by examiner

DEVICE FOR IRRADIATION OF THE EYE

CROSS-REFERENCE TO RELATED APPLICATIONS

The present application is a national phase entry under 35 U.S.C. § 371 of International Application No. PCT/US2015/067087, filed Dec. 21, 2015 and published on Jun. 30, 2016 as International Publication No. WO 2016/106210, which claims benefit of the filing date of U.S. Provisional Patent Application No. 62/095,416, filed Dec. 22, 2014, the disclosure of which is incorporated by reference herein.

BACKGROUND OF THE INVENTION

The present invention relates to systems, devices and methods for application of light to the cornea of an eye of a living subject as, for example, application of ultraviolet (UV) light to the cornea for corneal collagen crosslinking ("CCXL"). Commonly assigned U.S. patent application Ser. No. 14/314,518, filed Jun. 25, 2014 ("the '518 application"), published as U.S. 2014-0379054 A1, and U.S. Provisional Patent Application No. 61/839,016, filed Jun. 25, 2013 ("the '016 Provisional") disclose certain systems, devices and methods for this purpose. The disclosures of the '518 application and '016 Provisional are incorporated by reference herein As disclosed in the '518 application, a device for application of light to the eye may include a structure having a form and dimensions similar to those of a conventional scleral contact lens. The structure may include an optically scattering element, also referred to as an optically dispersive element, such as an optically scattering mass having an inner surface facing toward the eye. In use, the structure is placed on the eye of the patient, and light such as ultraviolet ("UV") light from a source such as a laser is directed into the device through a transmission optical fiber and passes into the scattering mass. As the light is dispersed within the mass, the scattered light passes through the interior surface of the mass and into the cornea.

The present invention provides still further improvements in devices of this general nature, and in systems and methods incorporating the same.

BRIEF SUMMARY OF THE INVENTION

One aspect of the invention provides a device for irradiation of the eye of a living subject. The device desirably includes a structure adapted to overlie the outer surface of the eye. The structure has an axis that extends in an axially inward or downward direction toward the eye when the structure overlies the eye. The structure includes a light scattering element disposed within the housing. The light scattering element includes a peripheral portion remote from the axis and a central axis adjacent the axis. The device further includes a plurality of transmission optical fibers in optical communication with the light scattering element at a plurality of locations spaced around the axis. For example, the structure may include an opaque peripheral wall extending around the axis and having a reflective inner surface facing toward the axis, as well as an opaque upper wall extending radially inward from adjacent the circumferential wall to adjacent the axis. The upper wall may have a downwardly facing reflective inner surface. The structure may further include an opaque lower wall below the upper wall. The inner wall desirably projects radially inward from the circumferential wall so that the upper wall, peripheral wall and lower wall cooperatively define a cavity. The lower wall desirably defines an aperture adjacent the axis for transmission of light from within the cavity to the eye. Each transmission optical fiber may have a distal end projecting into the cavity through the circumferential wall. The distal ends of the fibers may extend approximately tangential to a circle concentric with the axis.

The light scattering element may include an optically scattering mass disposed within the cavity and extending across the axis. Alternatively or additionally, the inner surfaces of the peripheral wall and the upper wall may be diffuse reflective surfaces, and the light scattering element may include these diffuse reflective surfaces.

The plural transmission fibers may form a bundle of fibers extending from the structure. A proximal end of the bundle may be coupled to a homogenizer fiber having a diameter larger than any individual one of the transmission fibers and desirably having a diameter equal to the diameter of the bundle as a whole. The homogenizer fiber desirably is adapted to transmit the light to be applied in multiple modes of transmission. A laser may be coupled to the end of the homogenizer fiber remote from the fiber bundle and structure. The homogenizer fiber will convert the coherent beam from a laser into an incoherent beam of substantially uniform intensity across its diameter, so as to provide substantially equal illumination to all of the individual transmission fibers.

As further explained below, preferred embodiments according to this aspect of the invention can provide a predictable pattern illumination through the aperture. In particular, preferred embodiments according to this aspect of the invention can provide illumination that is uniform in the circumferential direction around the axis. Moreover, certain preferred embodiments can provide these benefits in a structure that has a maximum thickness of a few millimeters or less.

DETAILED DESCRIPTION

Figure 1:
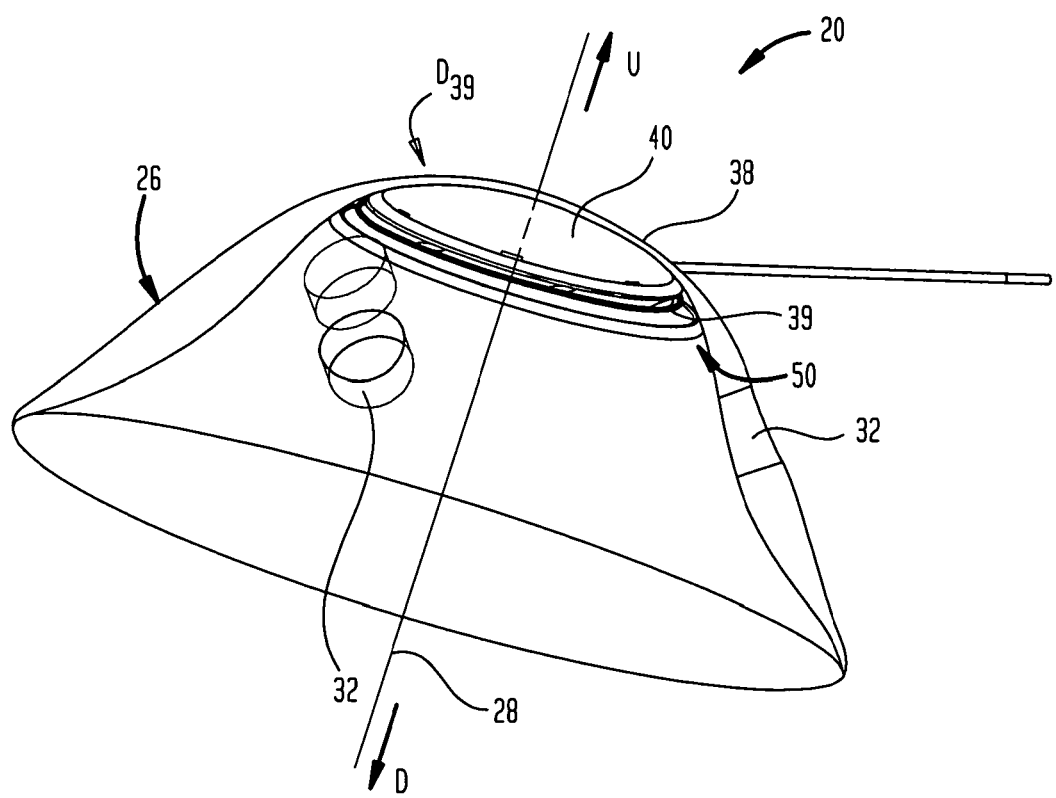
FIG. 1 is a partially phantom perspective view depicting a structure according to one embodiment of the invention.

A system according to one embodiment of the present invention, depicted in FIGS. 1-8 includes three primary components:

- A device 20 (FIG. 1) generally in the form and shape of a contact lens that delivers UV energy to the cornea
- A source 22 (FIG. 7) of UV energy and associated control components;
- A "homogenizer" 24 (FIG. 7) that helps ensure a uniform UV field is presented to the cornea.

In this embodiment, the device has a structure 20 which includes a housing 26 in the form of a scleral fit contact lens having a central axis 28. The housing is designed to engage the sclera S (FIG. 5) of the human eye so the axis 28 is coincident or nearly coincident with the axis of the eye through the cornea, iris and lens, and so that the central portion of the housing and the other components discussed below constituting the UV delivery system are at a clearance above the cornea to define a space 30 between the structure and the cornea when the structure is in place on the eye. The directions along axis 28 are referred to herein as the axially inward direction, which points toward the eye when the structure is in place on the eye, and the opposite, axially outward direction. The axially inward direction is also referred to herein as the downward direction D and the axially outward direction is also referred to herein as the upward direction U. Terms such as "above" and "below", as used herein with reference to features of the structure, should be understood as referring to this frame of reference, and not to the ordinary gravitational frame of reference.

Housing 26 may be made from a standard rigid gas permeable (RGP) material used in modern scleral lenses. For example, the housing may be formed from a fluorosilicone acrylate polymer such as that supplied by Bausch and Lomb under the designation "Boston Equalens II" or "Boston XO2." Scleral lens shapes are defined by a vault height, a base diameter, a central offset, and the shape of the scleral interface (haptic) surface. The housing used in this embodiment is a lens 21 mm in diameter at its base with an internal vault height (the distance along the axis 28 between the scleral contact surface and the central portion of the housing) of 6.5 mm. To ensure a secure fit with the sclera, the haptic surface is toric (not round) as the human eye tends to be off-round out as far as 21 mm. Three large fenestrations (32) extend through the housing so that the fenestrations will be in communication with the space 30 between the structure and the eye when the structure is in place on the eye. The housing has an additional fenestration 38 extending through the wall of the housing in a plane generally perpendicular to axis 28. The housing may have additional, smaller fenestrations (not shown) used for injection molding of a component during manufacture as discussed below.

The region of the housing surrounding axis 28 is referred to herein as the apex. The downwardly facing inside surface of the apex has a coating 40 that is reflective to UV light. The reflective coating may be formed by metallizing the area indicated in FIG. 2 with evaporated aluminum as a UV reflector. A flash coat of silicon dioxide ($SiO_2$) is put over the aluminum to keep it from oxidizing. Thus, the wall of the housing at the apex and the reflective coating 40 cooperatively constitute an upper wall 41 having a downwardly-facing inner surface formed by coating 40. The inner surface is reflective and opaque to the UV radiation to be applied during use of the structure. In this embodiment, the upper wall is also opaque to visible light. The downwardly-facing inner surface of this upper wall is concave. Stated another way, the center of the reflective surface, at axis 28, is above peripheral portions of the reflective surface.

Figure 2:
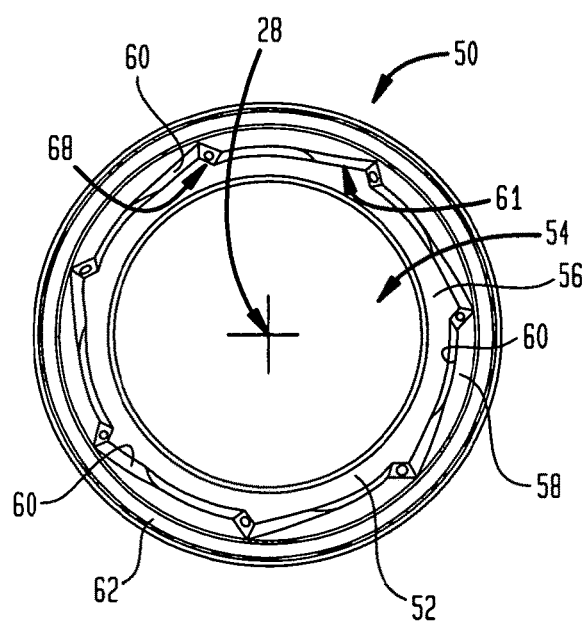
FIG. 2 is a diagrammatic plan view depicting a component of the structure shown in FIG. 1.
Figure 3:
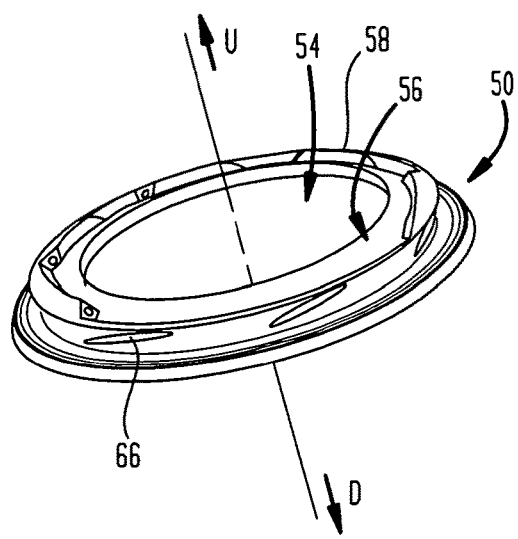
FIG. 3 is a diagrammatic perspective view of the component shown in FIG. 2.
Figure 4:
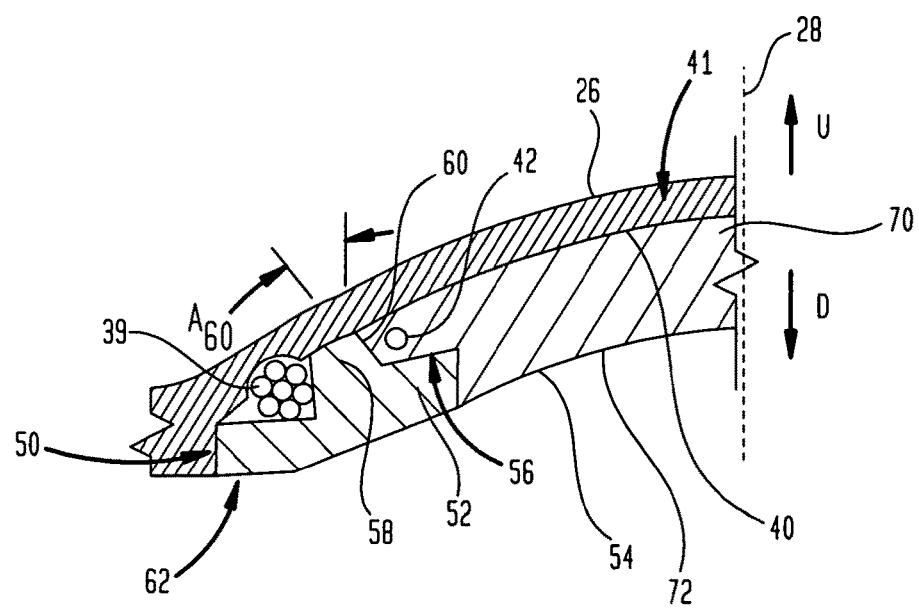
FIG. 4 is a fragmentary diagrammatic sectional view depicting certain components of the structure shown in FIGS. 1-3.

The device further includes a fiber carrier 50, best shown in FIGS. 2-4. The fiber carrier is made from a polymer. The fiber carrier may be formed by a process such as molding or stereolithography, commonly referred to as "3-D printing." The fiber carrier is a generally ring-like structure having a central axis that is coincident with the central axis 28 of the housing. Fiber carrier 50 includes a lower wall 52 projecting generally radially toward axis 28. The lower wall defines an aperture 54 centered on the axis. Lower wall 52 has an upwardly-facing inner surface 56 surrounding the aperture. As noted above, the upward direction U (FIGS. 3, 4) is the direction that will face away from the eye of the patient when the device is in place on the eye. The upward direction is the direction toward the reader in FIG. 2 In the particular embodiment depicted in FIGS. 1-4, the aperture is a circle concentric with axis 28, about 6 mm in diameter. The fiber carrier also has a peripheral wall 58 projecting upwardly from inner surface 56 of the lower wall remote from the aperture 54 and remote from axis 28. Portions of the peripheral wall are removed for purposes of illustration in FIG. 3. As best seen in FIG. 4, the peripheral wall 58 defines an inner circumferential surface 60 facing radially inwardly toward the central axis 28 and extending around the axis. This surface is generally in the form of a surface of revolution about the axis, but is notched at a plurality of locations 61 (FIG. 2), in this instance seven locations, equally spaced from one another around axis 28. The inner circumferential surface 60 may be tilted radially outwardly relative to the axis at a tilt angle $A_{60}$ at least in regions near the notches and near the fiber tips discussed below, so that the surface slopes away from the central axis 28 in the upward direction U. The upwardly facing inner surface 56 of the lower wall 52 can be coated with a metal such as aluminum as, for example, by vapor deposition. This coating desirably blocks light from passing through the fiber carrier, and optionally may make the upwardly facing surface reflective. Here again, the aluminum may be covered with a film of $SiO_2$ to protect it from oxidation. Optionally, the other surfaces of the carrier may be covered by a similar coating. Thus, the peripheral wall 58 may be opaque, and the inner surface 60 of the peripheral wall may be reflective.

The fiber carrier additionally has a flange 62 projecting radially outwardly beyond the peripheral wall 58. Openings extend through the peripheral wall. Each such opening has an external end 66 (FIG. 3) communicating with the external or radially outer circumferential surface of the peripheral wall and an internal end 68 (FIG. 2) communicating with the internal circumferential surface of the peripheral wall. Each opening extends along a line or curve that is approximately tangential to a circle around the central axis, but which slopes radially inwardly toward the central axis 28.

Figure 5:
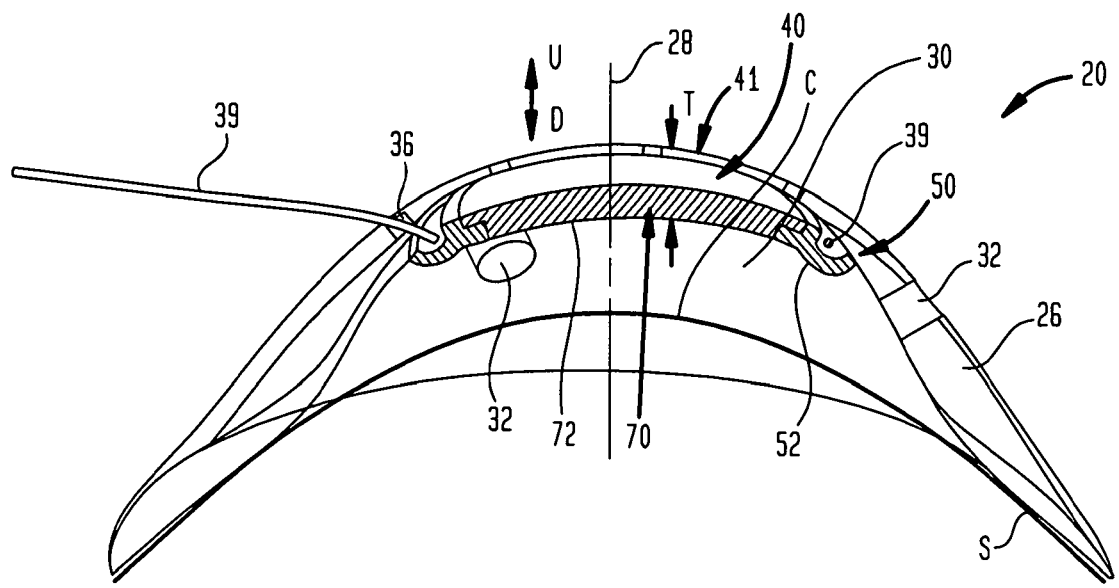
FIG. 5 is a diagrammatic partially sectional view of the structure shown in FIGS. 1-4.

As best seen in FIGS. 4 and 5, the fiber carrier is mounted in housing 26 with the lower wall 52 facing downwardly. The reflective inner surface 40 of upper wall 41 is disposed above the peripheral wall 58. Upper wall 41 is spaced apart from the lower wall 52. The upper and lower walls and the peripheral wall thus cooperatively define a cavity, and the aperture 54 defined by the lower wall communicates with this cavity.

The device further includes a mass of optically scattering material, also referred to as a diffuser 70 (FIGS. 4, 5) is disposed within this cavity and, in this embodiment, entirely fills the cavity and extends into the aperture 54. The diffuser is formed from a clear polymer such as a medical grade silicone or an epoxy having fine particles such as barium sulfate ($BaSO_4$) dispersed therein. For example, the diffuser may include about 1 to 10 weight percent barium sulfate. As disclosed in greater detail in the '518 application, the scattering properties of the material constituting the diffuser can be varied. The diffuser can be injection molded into place in housing 26.

As best seen in FIGS. 4 and 5, the diffuser is generally in the form of a dome-like shell having a lower surface 72 inwardly along axis 28 and an upper surface confronting the reflective coating 40 of the upper wall 41. As best seen in FIG. 4, a peripheral portion of the diffuser near the peripheral wall 58 is disposed between the upward-facing surface 56 of the fiber carrier lower wall and the reflective coating 40 on the upper wall 41 of the housing. A central portion of the diffuser, near the central axis, is aligned with the aperture in the fiber carrier.

Figure 6:
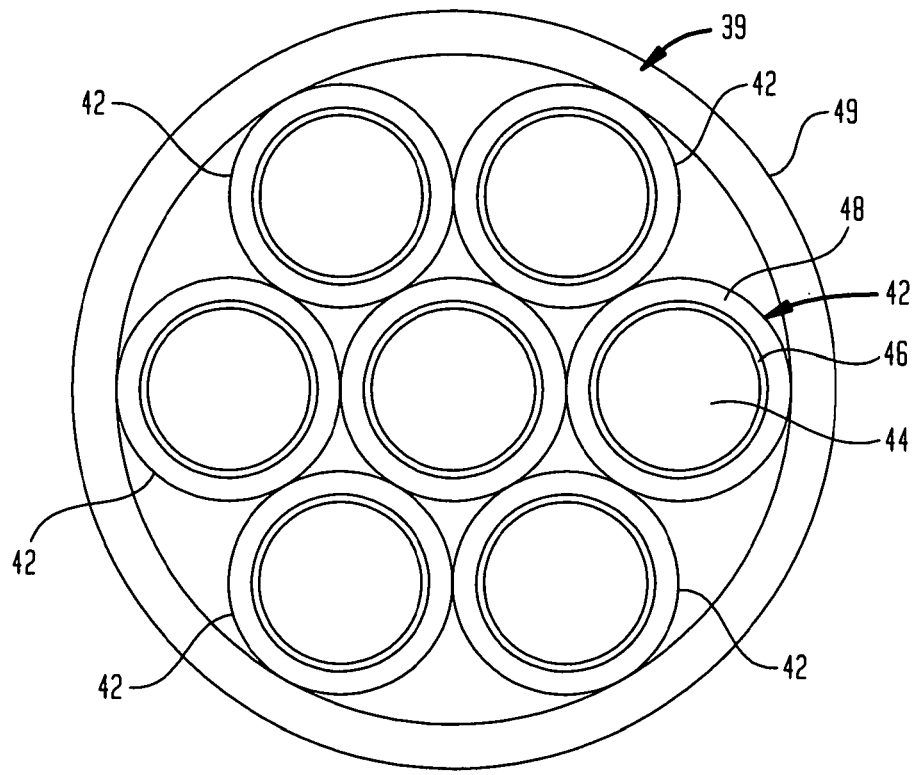
FIG. 6 is a sectional view of a component used in the structure of FIGS. 1-5.
Figure 7:
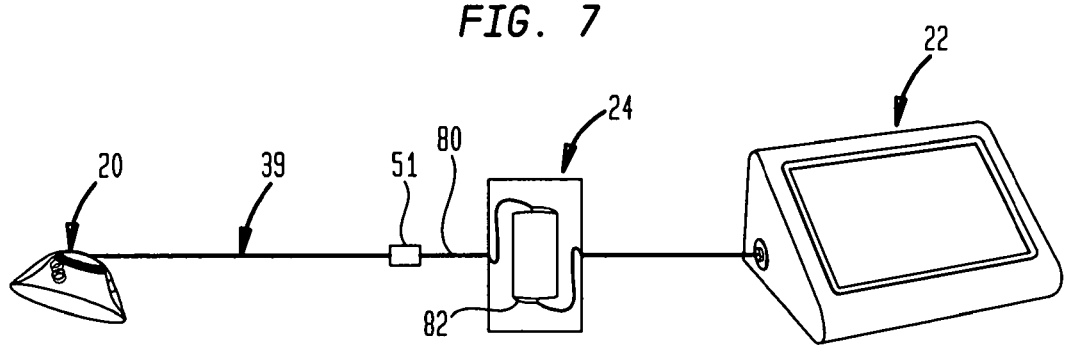
FIG. 7 is a block diagrammatic view of a system incorporating the structure of FIGS. 1-6.
Figure 8:
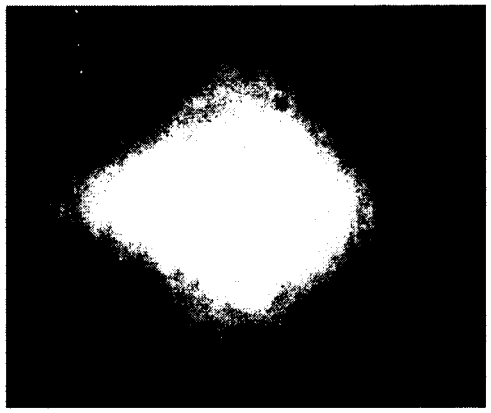
FIG. 8 is a pictorial representation of a light beam at one location within the system of FIG. 7.

The device further includes a bundle 39 of optical fibers 42 (FIG. 6). For example, the bundle may include seven fibers. Each fiber 42 may be a high tensile strength 50/55/65 fiber, which includes a core 44 of 50 μm diameter, a cladding 46 having an outer diameter of 55 μm, and a buffer coating having an outer diameter of 65 μm. Each fiber 42 is designed for transmitting UV. The small diameter of the individual fibers is desirable to enable each fiber to bend around a relatively small radius inside the fiber carrier. The 7 fibers are bundled together inside a protective jacket 49 formed from a medical grade polymer over most of the length of the bundle. The bundle extends from a distal end within structure 20 to an optical connector 51 (FIG. 7) at a proximal end of the bundle.

As best seen in FIG. 1, the distal end fiber bundle 39 wraps around the outside of the fiber carrier 50 in a circumferential direction $D_{39}$, so that the fiber bundle is disposed axially outward of the flange 62 on the fiber carrier. The distal end of the fiber bundle extends into the housing through fenestration 36 (FIG. 5). As best seen in FIG. 4, the flange of the fiber carrier is recessed downwardly relative to the upward facing surface 56 of the lower wall, so that the fiber bundle can be accommodated in the space within housing 26 axially outward of the flange. The jacket 49 is removed from the distal end of the fiber bundle which wraps around the fiber carrier. The distal tip of each individual fiber extends through one of the openings in the peripheral wall of the fiber carrier, from the external end 66 of the opening (FIG. 3) to and beyond the internal end 68 of the opening (FIG. 2), so that a tip of each fiber projects into the cavity between internal circumferential surface of the peripheral wall and the aperture, above the upwardly facing surface of the fiber carrier (FIG. 4). The tip of each fiber 42 is embedded in the peripheral portion of diffuser 70. Optionally, at the tip of each fiber, the buffer is removed and the end is shaped to facilitate passage of light out of the fiber. For example, each fiber may be rounded over or shaped into a ball, or may be provided with a polished flat surface. Alternatively, the buffer may be left intact to increase the structural integrity of the fiber tip.

The light source 22 (FIG. 7) is adapted to emit light at a wavelength such as UV or other wavelength that can activate a corneal crosslinking agent such as riboflavin. The light source may be part of a control console, which may also include components such as a power supply and controls. The light source may be a laser that emits a Gaussian shaped beam, with higher intensity in the center, decreasing toward the perimeter of the beam, as shown FIG. 8. In order to couple the laser into the 7 fiber bundle effectively so that each fiber carries roughly the same power, the Gaussian beam must be spread and homogenized.

The homogenizer 24 includes a homogenizer fiber 80 having a proximal end optically coupled to light source 22 and having a distal end coupled to the fiber bundle 39 at coupler 51. The homogenizer fiber has a core diameter larger than the core diameter of each individual fiber 42. For optimum coupling between the homogenizer fiber and the fiber bundle 39, the core diameter of the homogenizer fiber is equal to the diameter of the bundle. For example, the homogenizer fiber may be a 165/170/250 fiber (165 μm core, 170 μm diameter with cladding, 250 μm with acrylate buffer). At coupler 51, the buffer of the homogenizer fiber, the jacket of bundle 41 and the buffer layers 48 of the individual fibers are removed. Thus, the diameter of fiber bundle 39 within coupler 51 is 165 mm. The proximal ends of the fibers in the bundle and the distal end of the homogenizer fiber are polished to planar surfaces. The coupler holds the fiber bundle coaxial with the homogenizer fiber, and holds the polished surfaces together. The homogenizer fiber may have a plurality of bends remote from coupler 51. For example, these bends may be in the form of a plurality of coils 82 (FIG. 7) or a plurality of serpentine curves of alternating direction, formed by routing the homogenizer fiber around a series of pegs (not shown).

Figure 9:
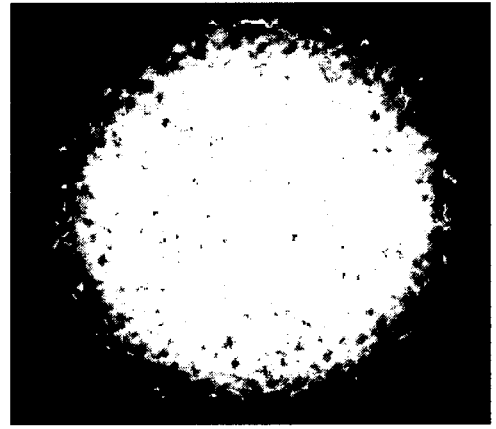
FIG. 9 is a representation of the light beam at a further location in the system of FIG. 7.

The light source 22 launches the Gaussian beam (FIG. 8) into the homogenizer fiber. The homogenizer fiber allows multiple spatial modes to propagate along its length. The bends in the fiber force the photons in the beam to bounce against the core cladding interface, hitting the interface at varying angles, with some photons remaining in the core and others entering and propagating in the cladding. This technique effectively creates multiple path lengths for the photons, and creates a beam of more uniform power density beam depicted in FIG. 9. In this process, the multi-mode propagation destroys the coherence of the laser beam, eliminating at least some "hot-spots" or high light intensity caused by the regular constructive and destructive interference pattern typical of lasers.

In operation, the structure 20 is placed on the eye of a patient, as schematically depicted in FIG. 5. The aperture 54 of the fiber carrier and the central portion of the diffuser overlie the cornea of the eye. Desirably, there is a space 30 between the inner surface of the diffuser and the cornea. This space may be filled with a liquid by means of the fenestrations 32 in the housing. For example, a source of a liquid (not shown) may be connected to one of these fenestrations, and fresh liquid may be supplied while the device remains in place on the eye. This helps to keep the cornea moist. As disclosed in the commonly assigned U.S. Provisional Patent Application No. 62/095,288, filed Dec. 22, 2014, the disclosure of which is incorporated by reference herein, the cornea may be maintained in an oxygenated condition during application of light by supplying a liquid that contains a source of oxygen. Additionally, the housing may be formed from an oxygen-permeable material. Desirably, the cornea is exposed to a liquid that contains a crosslinking agent such as riboflavin before applying the crosslinking light. This may be done by applying a liquid containing the crosslinking agent through the fenestrations in the housing before applying light, or by applying the agent before placing the structure on the eye.

While the device is in place on the eye, the light source 22 is activated to direct light through the homogenizer fiber and coupler into the fiber bundle 39. The light passes along the individual fibers to the tips of the fibers embedded in the peripheral region of the diffuser. Light passing out of the fibers spreads inwardly toward the central axis. Some of the light passing out of the fiber tips will be directed upwardly or downwardly. The upward facing surface 56 of the fiber carrier lower wall and the downward facing reflective inner surface 40 of the housing will help to redirect this light toward the central axis. As the light passes through the diffuser, it will be scattered. Some of the dispersed light will pass downwardly and thus pass into the cornea. Dispersed light that is directed upwardly will be reflected by the reflective surface of the housing, and thus will also pass into the cornea.

The multiple fiber ends provide illumination from plural sources around the circumference of the diffuser, which helps to provide illumination which is uniform in the circumferential direction around axis 28 over the entire central region of the diffuser and thus illumination which is uniform in the circumferential direction over the area of the cornea aligned with the aperture. This in turn helps to provide uniform crosslinking of the cornea. The reflective surfaces of the fiber carrier and housing also promote uniform illumination. The illumination may be uniform in the radial direction. Alternatively, the intensity of the light at the periphery is intentionally slightly elevated from the intensity near the axis, as this can help achieve uniform crosslinking of the cornea.

The structure, including the housing, fiber carrier, fibers and diffuser together, may form a thin shell having a form corresponding to a conventional scleral contact lens. For example, the structure, including the housing and the components disposed within the housing may be in the form of a shell having a thickness less than about 3 mm thick, and preferably less than about 1 mm thick. The thickness dimension is the dimension T (FIG. 5) from inside the shell to outside the shell, measured in the direction perpendicular to the exterior surface of housing 26. As discussed in the '518 application, the small thickness of the shell allows the patient to close his or her eye during the treatment.

Figure 10:
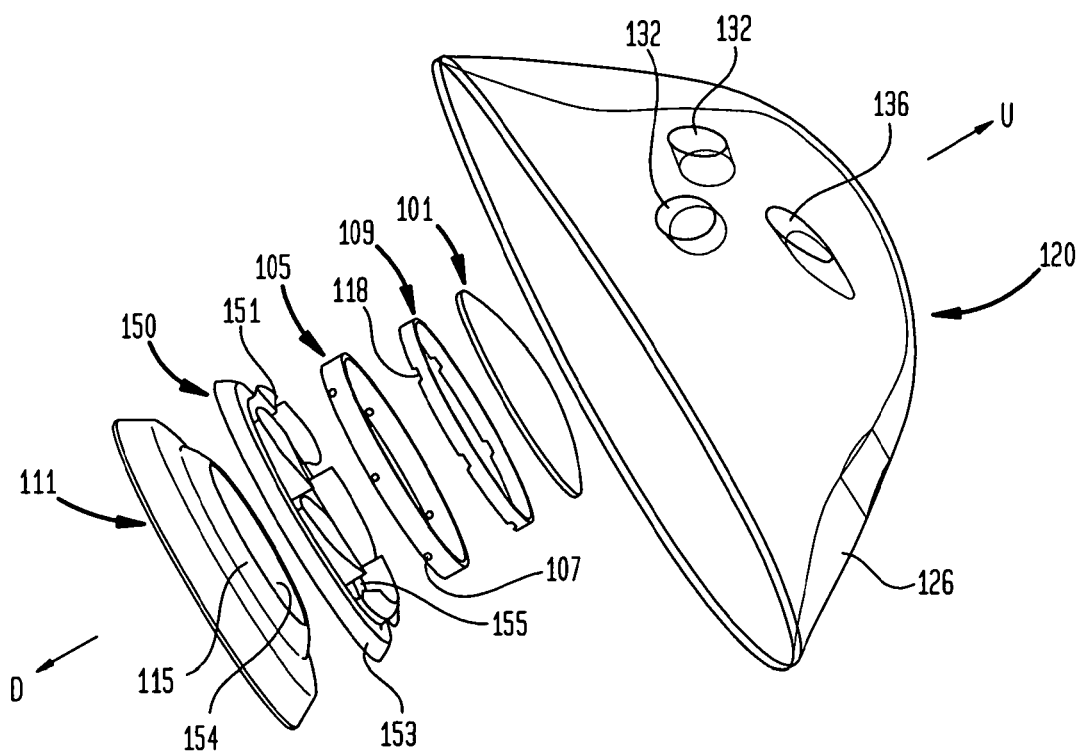
FIG. 10 is an exploded view depicting certain components used in a structure according to a further embodiment of the invention.

A structure 120 according to a further embodiment of the invention (FIG. 10) includes a housing 126 generally similar to the housing 26 discussed above. The housing has fenestrations 132 similar to the fenestrations discussed above and an additional fenestration 136 for passage of a fiber bundle as discussed above. Here again, the housing has a metallic coating 140 on the downwardly facing surface of the apex, adjacent the central axis 128 of the housing. Here again, the metallic film may be an aluminum film and may be covered with a layer of a silicon oxide to protect the metallic film. A cap 101 in the form of a shallow dome conforming to the inner surface of the housing covers the metallic film 140. Cap 101 is formed from a polymer film. The film is highly reflective to the light to be applied, such as UV light in the 360 nm to 380 nm wavelength range, and provides diffuse reflectivity. For example, films suitable for providing diffuse reflection of ultraviolet and blue light are commercially available from Whiteoptics LLC of New Castle, Del. The cap may be thermoformed to the dome shape shown in FIGS. 10 and 11. Cap 101, metallic layer 140, and the overlying portion of housing 126 cooperatively constitute an upper wall 140, with film 101 defining the downwardly facing surface of the wall. Here again, the downwardly facing inner surface 103 of the upper wall is concave.

Figure 11:
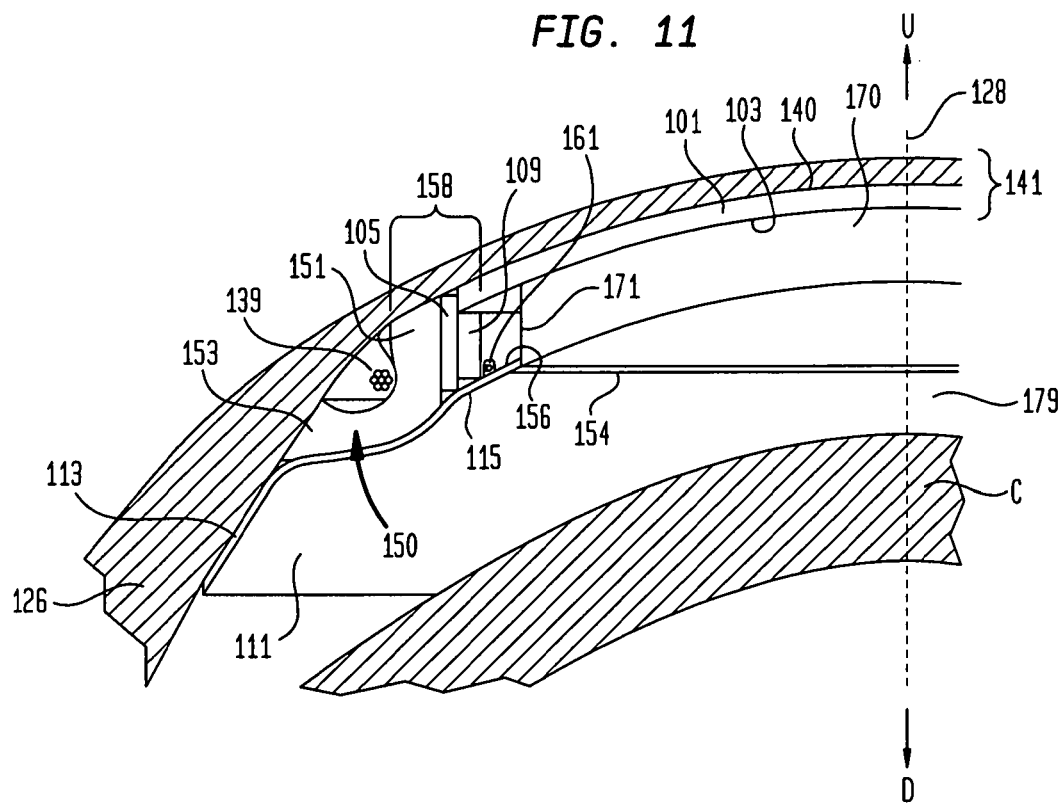
FIG. 11 is a fragmentary sectional view depicting the structure of FIG. 10.
Figure 12:
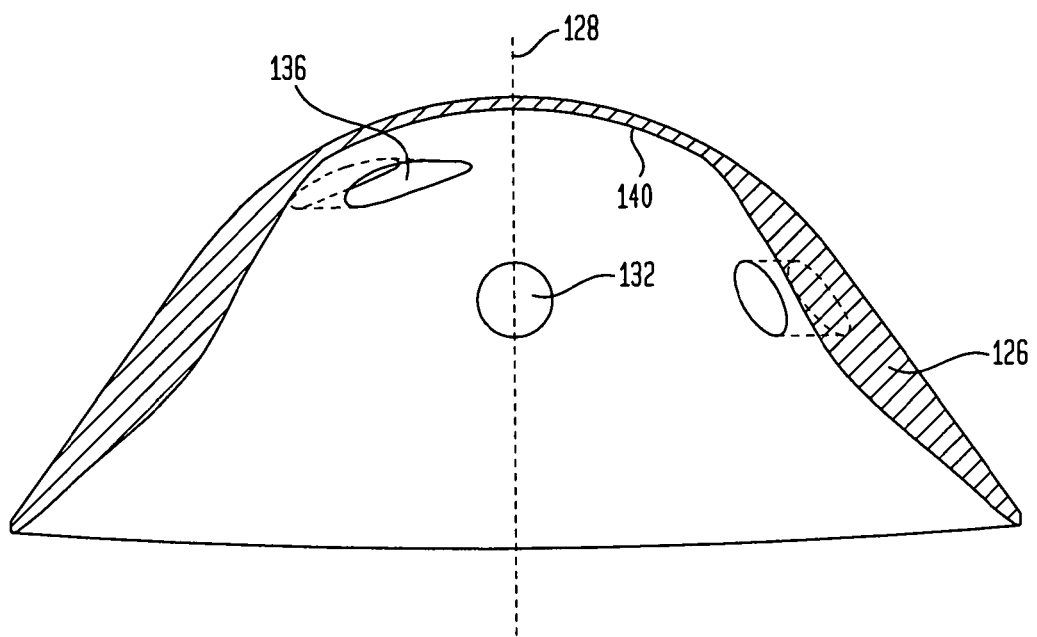
FIG. 12 is a sectional view depicting a component used in the structure of FIGS. 10 and 11.

The structure further includes a fiber carrier 150 formed from a polymeric material. Fiber carrier 150 is generally in the form of a ring with a central opening and a series of projections 151 surrounding the central opening and projecting upwardly from the remainder of the fiber carrier. The fiber carrier includes a flange 153 projecting radially outwardly from the projections. As best seen in FIG. 11, flange 153 is disposed at the lower end of the projections. Slots 155 (FIGS. 10, 13) extend between the projections. In this embodiment, seven equally-spaced slots 155 and seven projections 151 are provided around the circumference of the fiber carrier. An opaque metallic light blocking ring 105, such as a short section of stainless tubing, is provided with small openings 107, such as small holes or slots, extending through the wall of the tube. Ring 105 is opaque. A ring 109 formed from a UV reflective film similar to that used to make cap 101 is also provided. Ring 109 has slots or holes 118 at its lower edge. The radially outer surface of ring 109 may be coated with a vapor deposited layer of aluminum, which can be protected from corrosion and optimized for UV reflectance with a layer of a transparent coating material such as a silicon monoxide or dioxide. The holes or slots 107 and 118 may extend through rings 105 and 109 in directions which are oblique to the radial directions of the rings, preferably closer to the tangential directions of the rings than to the radial directions.

Figure 13:
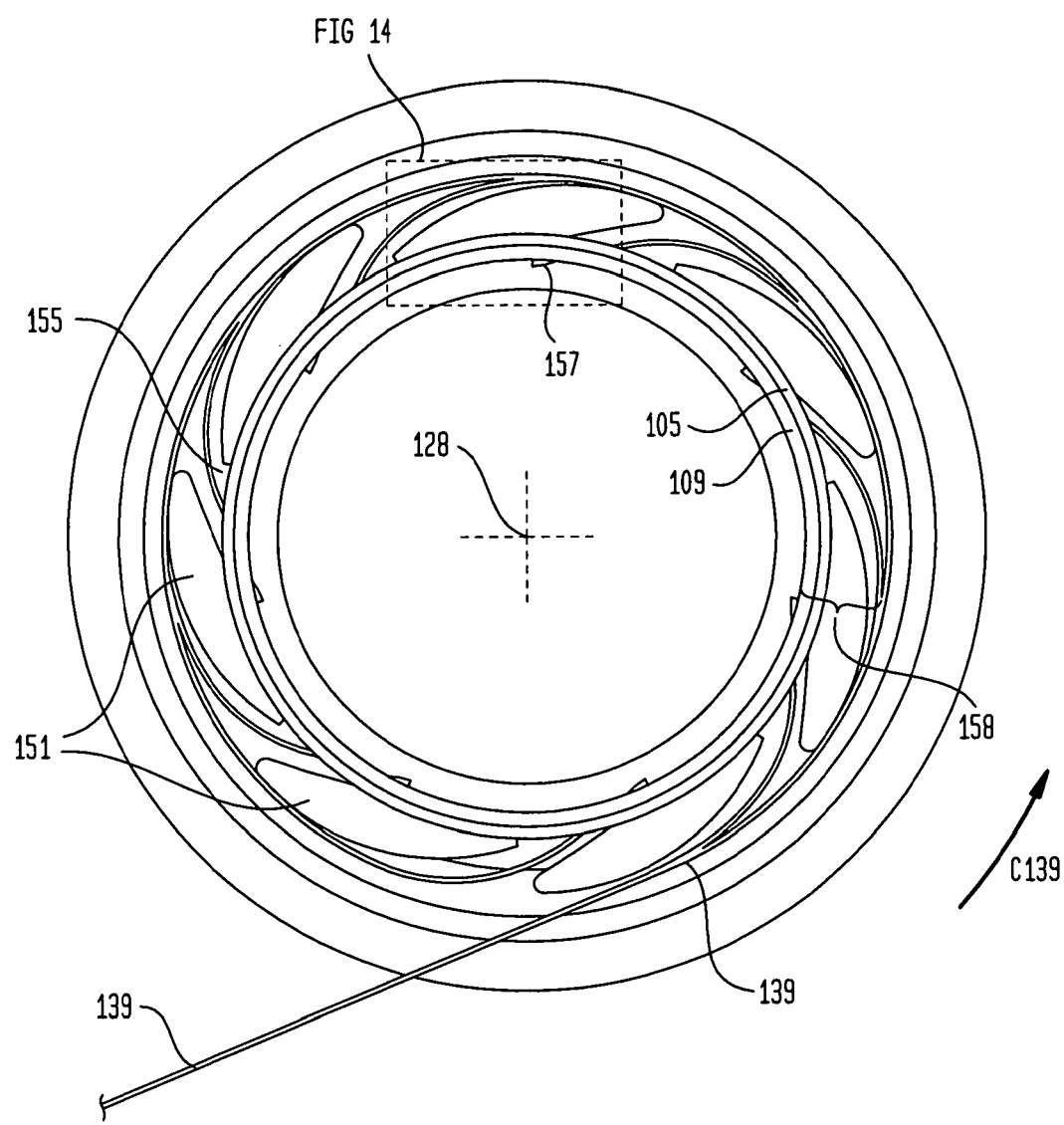
FIG. 13 is a diagrammatic plan view depicting certain other components used in the structure of FIGS. 10-12.

As best seen in FIG. 13, metallic light blocking ring 105 is disposed radially inward of projections 151 on the fiber carrier, and reflective film ring 109 is disposed inside the metallic light blocking ring 105. The openings 107 in the metallic light blocking ring and openings 118 in the film ring 109 are aligned with one another and with slots 155 in the fiber carrier. The projections 151 of the fiber carrier, the metallic light blocking ring 105, and film ring 109 thus form a composite peripheral wall. The peripheral wall is in the form of a cylinder, with the radially inner surface of the cylinder being defined by film ring 109. The fiber carrier, metallic ring, and film ring are mounted in housing 126 so that the peripheral wall encircles the central axis 128 of the housing and is coaxial therewith.

The structure according to this embodiment further includes an opaque metallic bottom ring 111. For example, the bottom ring may be formed from a sheet or foil of a metal such as stainless steel or aluminum about 50 µm thick. The bottom light blocking ring includes a peripheral section 113 generally conforming in shape to the interior of housing 126 and a central section 115 defining a circular aperture 154. The central section 115 defining aperture 154 slopes upwardly in the radially inward direction. The light blocking ring 111 is mounted within the housing below fiber carrier 150 so that the central portion 115 of the light blocking ring projects radially inward from the peripheral wall 158. The central portion 115 of the light blocking ring constitutes a lower wall. The upwardly facing surface 158 of this lower wall desirably is reflective to the light to be applied. Lower wall 115 projects radially inwardly and upwardly from a juncture with the peripheral wall 158. In this embodiment as well, the lower wall 115, peripheral wall 158, and upper wall 141 cooperatively define a cavity, and aperture 154 communicates with the cavity.

A dome-shaped diffuser 170 is disposed within the cavity in alignment with aperture 154. Diffuser 170 may be formed from an optically scattering transparent or translucent material as discussed above. In this embodiment, the radially outer or peripheral edge 171 of diffuser 170 is remote from central axis 128, but is spaced radially inwardly from peripheral wall 158. A fiber bundle 139, identical to the fiber bundle 39 discussed above, extends into housing 126 through fenestration 136. Here again, the distal end of the fiber bundle is positioned above flange 153 and wraps around the fiber carrier and around the peripheral wall 158 in a circumferential direction $C_{139}$. The individual fibers from the bundle extend through the peripheral wall via the slots 155 in the fiber carrier and the openings 107 and 118 in the light blocking ring 105 and film ring 109.

Figure 14:
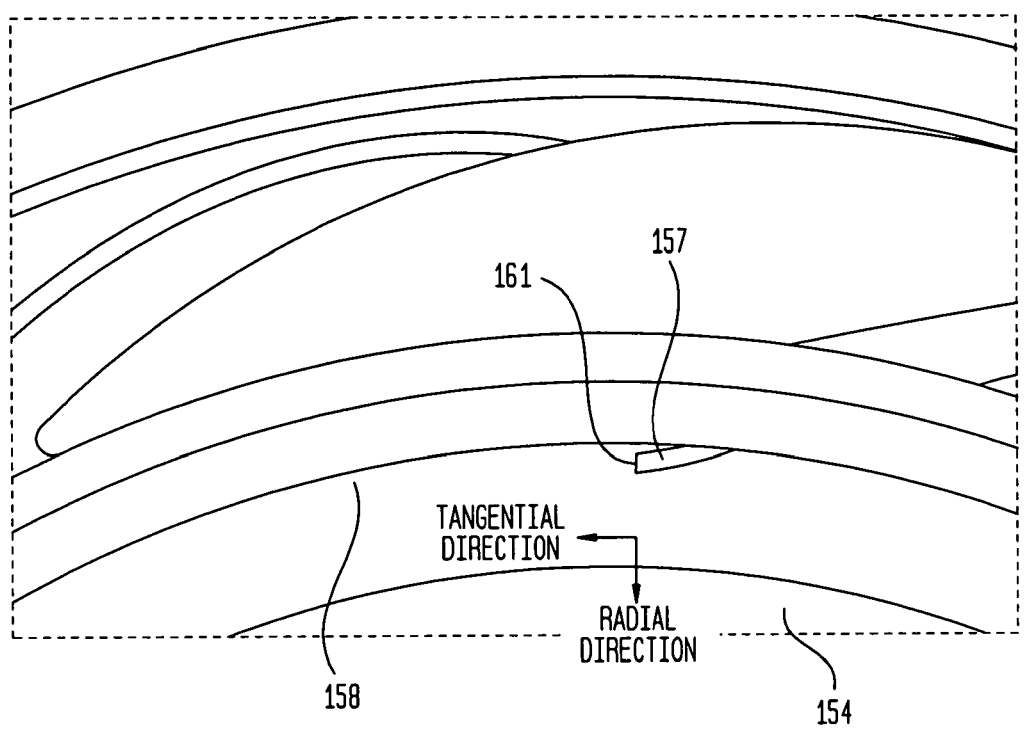
FIG. 14 is a fragmentary view on an enlarged scale of the area indicated in FIG. 13.

Here again, the distal tips 157 of the individual fibers are disposed at equally spaced intervals around a circle concentric with axis 128. As best seen in FIGS. 13 and 14, the distal tip (FIG. 14) of each fiber projects only slightly (ideally less than 0.2 mm) beyond the inward surface of the reflective wall 109 and into the cavity. The axis of each fiber tip points in a direction which is nearly tangential to the inner surface of the peripheral wall 158. Light emanating from the distal extremity of the fiber tends to spread in a cone. Pointing the fiber tip 157 in a roughly tangential direction (as opposed to pointing it radially inward toward the axis 128), helps diffuse the light that eventually exits the aperture 154 by preventing this light cone from directly entering the aperture. Instead, the light cone is forced to intersect a large area on the circumferential diffuse reflective peripheral wall.

As best seen in FIG. 11, the distal extremity 161 of each fiber is disposed radially outwardly of diffuser 170 rather than embedded therein. Moreover, the distal extremity of each fiber is disposed adjacent the bottom of wall 158 and adjacent the juncture of the peripheral wall 158 and lower wall 115. Thus, the lower wall 115 slopes upwardly from the distal extremities of the fiber to aperture 154. This arrangement also helps to assure that light will not spread directly from the distal extremities of the fiber into the aperture.

Figure 15:
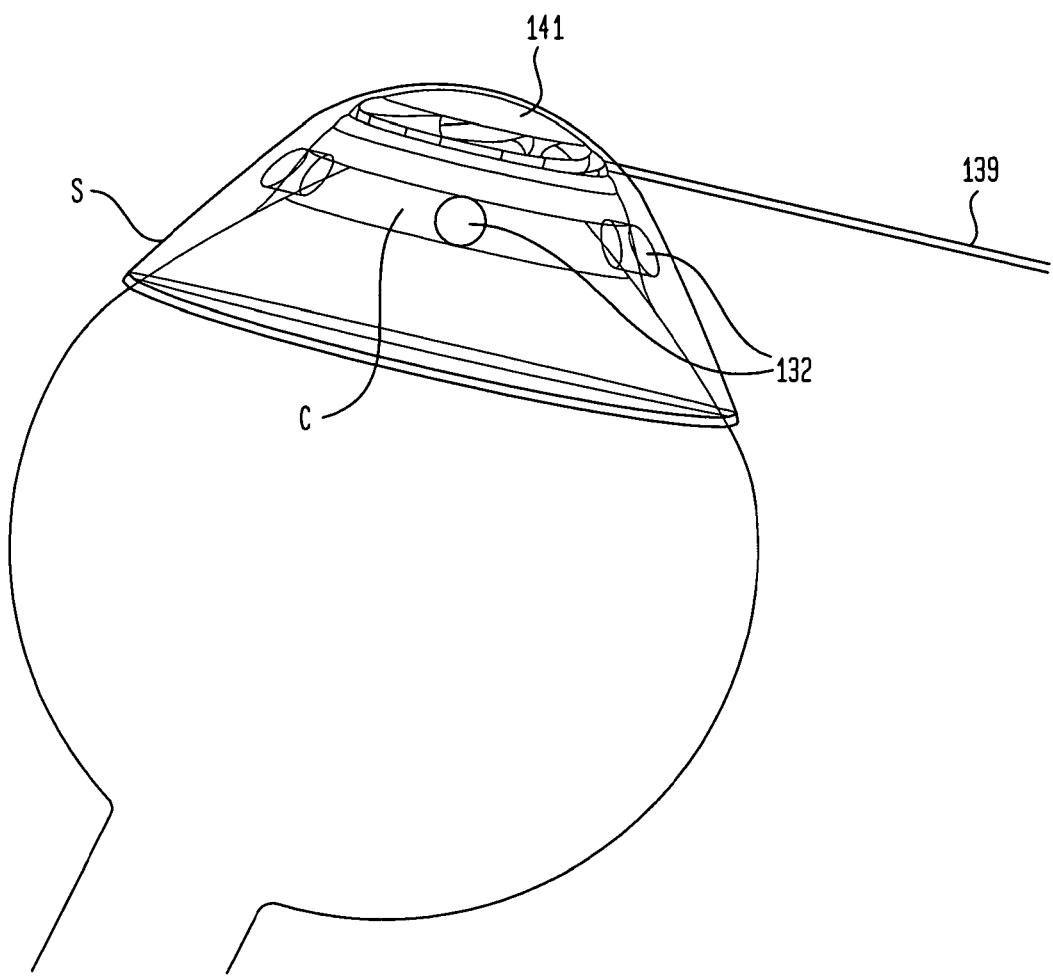
FIG. 15 is a diagrammatic phantom view of the structure shown in FIGS. 10-14.

The structure 120 is used in the same manner as discussed above. Here again, the proximal end of fiber bundle 139 is connected to a homogenizer and light source as discussed above. The structure is placed on the eye of a subject as shown in FIG. 15. The bottom ring 111, fiber carrier, and diffuser are all disposed above the cornea C of the eye, with the haptic or scleral contact surface at the bottom of housing 126 contacting the sclera. Here again, there is a space 179 between the structure and the cornea C (FIG. 11). The fenestrations 132 in the housing communicate with this space so that liquid can be introduced into this space.

Once again, light is applied through fiber bundle 139. Light emanating from the distal extremities of the fibers encounters the diffuse reflective surface of the peripheral wall 158 where it is scattered and reflected radially inwardly and upwardly toward diffuse reflective surface of the upper wall 141 and downwardly through aperture 154 into the cornea. Some of the light emanating from the fibers will be reflected by the inner surface 156 of lower wall 115. This surface is oriented and positioned to reflect light into the diffuse reflective surfaces of the peripheral wall and upper wall. In this embodiment, the light scattering element includes the diffuse reflective surfaces of the peripheral wall and upper wall, in addition to the diffuser. Here again, the optical fibers are in communication with a peripheral portion of the light scattering element. Additional scattering may be provided by diffuser 170. The upper wall 141 is opaque due to the presence of metal layer 140, and the peripheral wall 158 is opaque due to the presence of light blocking ring 105. These opaque walls protect the patient's eyelid from the UV light applied during the treatment. Likewise, the opaque bottom light blocking ring 111, and particularly the opaque lower wall, protects the sclera and other structures in the eye from the UV light. In a variant of this approach, diffuser 170 may be replaced by a clear transparent element without light scattering properties.

A structure according to a further embodiment (FIG. 16) is similar to the structure discussed above with reference to FIGS. 10-15. In this embodiment, however, the diffuser is replaced by a diffusing window 270 extending across the aperture 254. For example, window 270 may be formed from a polymer having embedded particles and having diffusing properties, or may be formed as a transparent body with small surface features. The window is generally dome-shaped but has flat, ring-like ledge 271 projecting outwardly from the aperture above the distal extremities 261 of the fibers. A space below ledge 271 is filled with a light scattering material 273 to provide additional light diffusion around the distal extremities of the fibers.

The upwardly facing surface of lower wall 215 desirably is reflective. The light scattering material 273 and scattering ledge 271 help to scatter light passing upwardly from the extremities of the fiber and light reflected by the lower wall. Here again, the light scattering element includes the diffuse reflective surfaces of the peripheral wall 258 and top wall 241.

Figure 16:
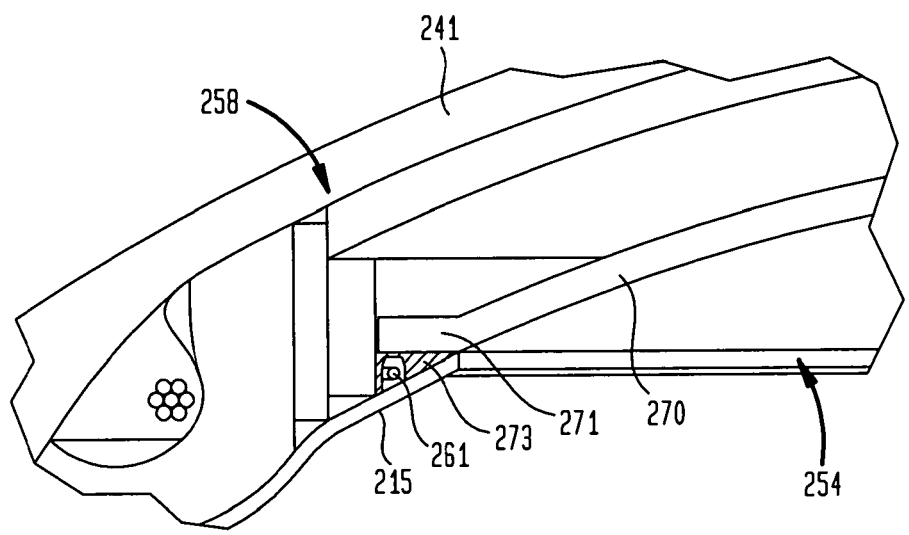
FIGS. 16 and 17 are fragmentary sectional views depicting certain components of structures according to further embodiments of the invention.
Figure 17:
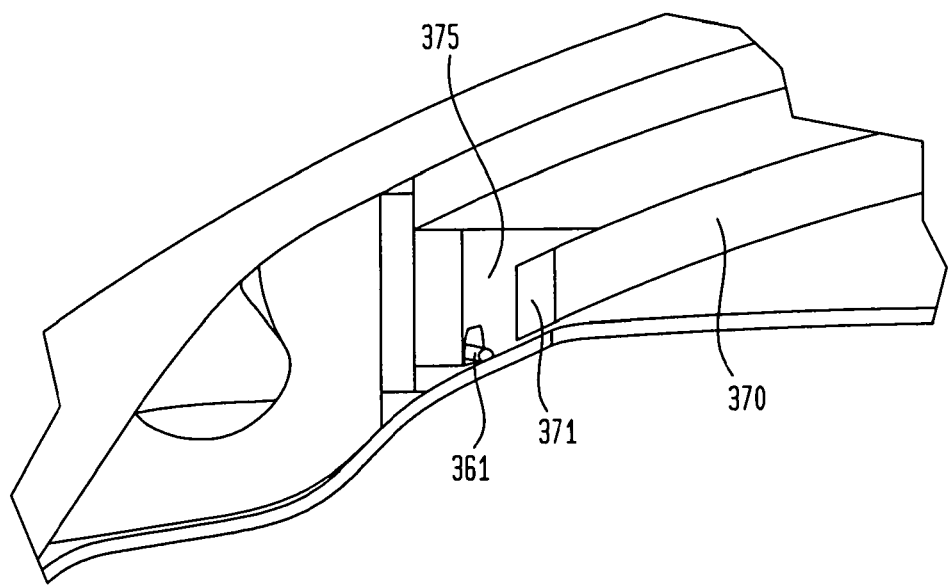
Figure 18:
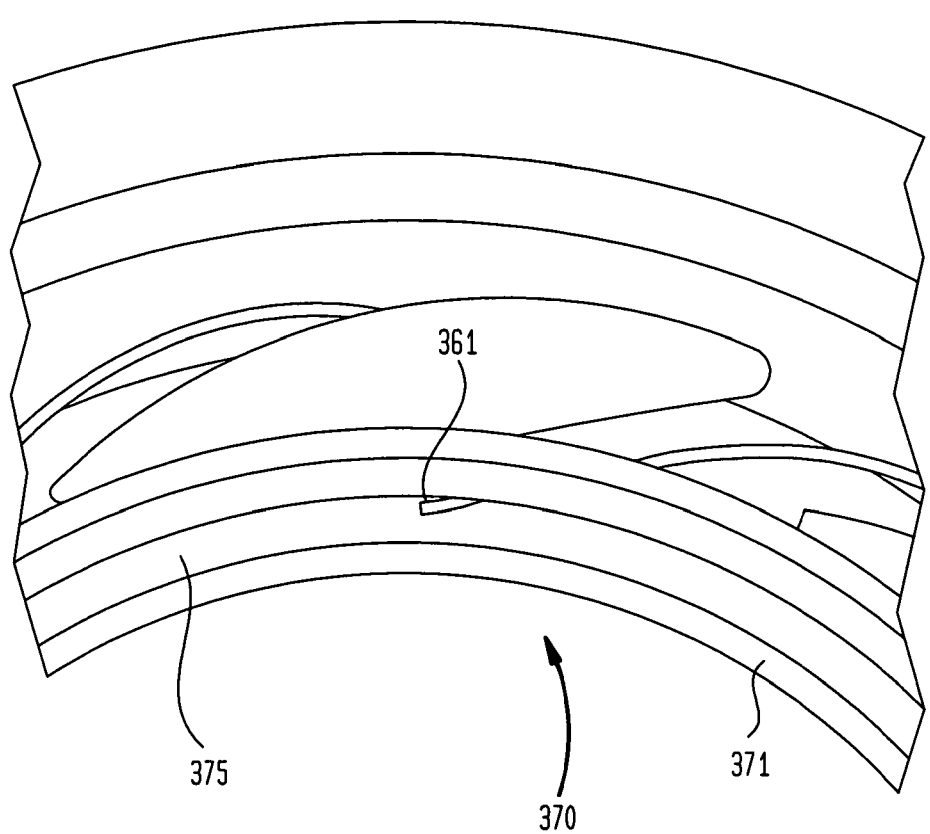
FIG. 18 is a fragmentary plan view depicting portions of the structures shown in FIG. 17.

A structure according to yet another embodiment (FIGS. 17, 18) is similar to the structure shown in FIG. 16. In this structure, the window 370 incorporates a substantially opaque baffle 371 at its radially outer edge. Baffle 371 further blocks light propagating from the distal extremities 361 of the fibers in directions nearly perpendicular to the central axis, which helps to promote more effective scattering by the diffuse reflecting surfaces of the peripheral and top walls. In variants of the approaches in FIGS. 16 and 17, the windows 270 and 370 may be formed from non-scattering transparent material, so that scattering is achieved primarily by the diffuse reflective surfaces. In other variants, the space 375 between the baffle 371 and the peripheral wall 258 is filled with a diffusing material such as an epoxy with BaSO4 scatters embedded.

The features discussed above can be varied. For example, the number of fibers and fiber ends can be varied. Also, it is not essential that the fibers be bundled with one another or connected in common to the same light source. The homogenizer discussed above may be omitted. It is not essential to provide uniform illumination in the various fibers. For example, the fibers may be spaced at non-uniform intervals around the central axis, with those fibers receiving less illumination being spaced at closer intervals. Also, as discussed in the '518 application, the aperture need not be circular, but instead may be patterned to provide other patterns of illumination. For example, a circular aperture can be used, for example, to treat myopia. For treatment of hyperopia, the lower wall may include an opaque portion at the axis and remote from the axis, with an annular an annular slot encircling the opaque portion at the axis. For treatment of astigmatism, the aperture may include openings in the lower wall spaced apart from one another in the circumferential direction around the axis. A translucent or transparent diffuser may have non-uniform properties as, for example, varying extinction length as discussed with reference to FIG. 22 of the '518 application. In some embodiments, the concentration of scattering particles is varied in the radial direction. For example, a diffuser may contain more scatting particle near the axis and fewer near the periphery as a means to control the intensity of the light that exits the aperture. Also, a translucent or transparent diffuser need not incorporate particles. For example, the diffuser may have surface irregularities which act to scatter light. Diffuse reflective surfaces can be provided by elements other than the polymeric films discussed above. For example, reflective elements such as metallic elements having rough surfaces may be used.

The fiber bundle may wrap around the axis in opposite directions in devices to be used for the opposite eye. For example, the bundle may wrap counter clock-wise (when looking at the patient) for a device to be used in the left eye, and clock-wise for the right eye. This is done to allow the bundle to comfortably lead away from the patient.

The features of the various embodiments may be combined with one another. For example, the diffuse reflective surfaces can be used in all of the embodiments discussed herein. In any of the embodiments discussed above, the lower wall may be formed integrally with the fiber carrier or provided by a separate element.

The invention claimed is:

1. A device for irradiation of the eye of a living subject, the device comprising a structure adapted to overlie the outer surface of the eye, the structure having an axis extending in a downward direction towards the eye and extending through the cornea, iris and lens of the eye when the structure overlies the eye, a light scattering element within the structure, the light scattering element including a peripheral portion remote from the axis and a central portion extending across the axis, and a plurality of transmission optical fibers having distal ends in optical communication with the peripheral portion of the light scattering element at a plurality of locations spaced around the axis, the distal ends of the transmission optical fibers extending approximately tangential to a circle concentric with the axis, wherein the structure includes:
   (i) an opaque peripheral wall extending around the axis having a reflective inner surface facing toward the axis;
   (ii) an opaque upper wall extending from adjacent the peripheral wall to adjacent the axis, the upper wall having a reflective inner surface facing downwardly; and
   (iii) an opaque lower wall spaced from the upper wall, the lower wall projecting radially inwardly from the peripheral wall so that the upper wall, peripheral wall and lower wall cooperatively define a cavity, the lower wall defining an aperture adjacent the axis for transmission of light from the cavity to the eye.

2. A device as claimed in claim 1 wherein the plural transmission optical fibers constitute a fiber bundle extending out of the structure.

3. A system comprising a device as claimed in claim 2 and a homogenizer including a homogenizer fiber having a diameter larger than the diameter of each said transmission optical fiber, the homogenizer fiber being adapted for multimodal transmission of light, the fiber bundle having a proximal end coupled to a distal end of the homogenizer fiber.

4. A system as claimed in claim 3 further comprising a laser coupled to a proximal end of the homogenizer fiber, the homogenizer fiber being adapted to provide multi-mode transmission of light emitted by the laser.

5. A system as claimed in claim 4 wherein the laser is adapted to emit ultraviolet light.

6. A device as claimed in claim 1 wherein the distal ends of the transmission optical fibers project into the cavity through the peripheral wall.

7. A device as claimed in claim 6 wherein the lower wall slopes upwardly from a juncture with the peripheral wall and wherein the lower wall has a reflective surface facing upwardly, and wherein the transmission optical fibers have distal extremities disposed adjacent the juncture so that the lower wall extends upwardly beyond the extremities of the fibers.

8. A device as claimed in claim 7 further comprising an opaque baffle disposed within the cavity at a radial location between the distal extremities of the fibers and the aperture.

9. A device as claimed in claim 7 wherein the light scattering element includes an optically scattering transparent or translucent element disposed between the peripheral wall and the lower wall.

10. A device as claimed in claim 6 wherein the inner surfaces of the peripheral wall and upper wall are diffuse reflective surfaces and wherein the light scattering element includes the diffuse reflective surfaces.

11. A device as claimed in claim 6 wherein the light scattering element includes a scattering mass disposed within the cavity.

12. A device as claimed in claim 11 wherein the scattering mass extends across the axis.

13. A device as claimed in claim 6 wherein the light scattering element includes a scattering window extending across the aperture.

14. A device as claimed in claim 6 wherein the plural transmission fibers constitute a bundle, and wherein the bundle at least partially encircles the peripheral wall, with the distal ends of the fibers extending from the bundle through the peripheral wall at circumferentially-spaced locations so that the number of fibers in the bundle diminishes in a circumferential direction.

15. A device as claimed in claim 14 wherein distal ends of the plural transmission fibers are substantially equally spaced from one another.

16. A device as claimed in claim 6 wherein the structure includes
   (i) a fiber carrier having an opening encircling the axis and a peripheral wall encircling the opening and
   (ii) an opaque ring disposed within the opening defined by the peripheral wall, the peripheral wall of the fiber carrier and the ring cooperatively constituting at least a portion of the peripheral wall of the structure.

17. A device as claimed in claim 16 wherein the structure further includes a film reflective to ultraviolet light disposed within the ring and overlying an inner surface of the ring, the peripheral wall of the structure further including the film.

18. A device as claimed in claim 17 wherein the ring has openings extending through it and the film has openings extending through it in alignment with the openings in the ring, and wherein the distal ends of the transmission fibers extend through the aligned openings in the ring and the film.

19. A device as claimed in claim 1 wherein the inner surface of the upper wall is concave.

* * * * *